US005487747A

United States Patent [19]

Stagmann et al.

[11] Patent Number: 5,487,747
[45] Date of Patent: Jan. 30, 1996

[54] OPTHALMIC SURGICAL APPARATUS FOR MACERATING AND REMOVING THE LENS NUCLEUS FROM THE EYE OF A LIVING BEING

[75] Inventors: Robert Stagmann, Pretoria, South Africa; Rudolf Demmerle, Schaffhausen, Switzerland

[73] Assignee: Grieshaber & Co. AG Schaffhausen, Schaffhausen, Switzerland

[21] Appl. No.: 237,707

[22] Filed: May 3, 1994

[30] Foreign Application Priority Data

May 7, 1993 [CH] Switzerland ............. 01470/93
Apr. 9, 1994 [CH] Switzerland ............. 01042/94

[51] Int. Cl.[6] ........................................ A61B 17/32
[52] U.S. Cl. .................. 606/166; 606/170; 606/180; 604/22
[58] Field of Search ................... 606/166, 167, 606/170, 171, 177, 178, 180, 159; 604/22

[56] References Cited

U.S. PATENT DOCUMENTS

| 4,631,052 | 12/1986 | Kensey | 604/22 |
| 4,681,106 | 7/1987 | Kensey | 604/22 X |
| 4,747,821 | 5/1988 | Kensey | 604/22 |
| 5,019,088 | 5/1991 | Farr | 606/180 X |
| 5,063,942 | 11/1991 | Kilmer et al. | 606/166 X |
| 5,112,299 | 5/1992 | Pascaloff | 606/180 X |
| 5,154,694 | 10/1992 | Kelman | 606/171 X |
| 5,320,627 | 6/1994 | Sorensen et al. | 606/170 X |

FOREIGN PATENT DOCUMENTS 2365891  9/1976  Germany ............. 606/166

Primary Examiner—Stephen C. Pellegrino
Assistant Examiner—Michael Peffley
Attorney, Agent, or Firm—Henry M. Feiereisen

[57] ABSTRACT

An ophthalmic surgical device for macerating the lens nucleus in the eye and for removing particles of the macerated lens nucleus from the eye of a living being, includes a hand-held housing with a head piece attached at one axial end of the housing and supporting a guide tube. Disposed in the guide tube is a tubular probe which is operatively connected to a motor drive and projects beyond the guide tube with its tip to carry a cutting element in form of at least two rotatable wing-like blades oriented approximately transversely to the longitudinal axis of the guide tube. By means of the drive, the tubular probe is rotatable relative to the stationary guide tube about the longitudinal axis and movable at a high frequency in direction of the longitudinal axis.

23 Claims, 7 Drawing Sheets

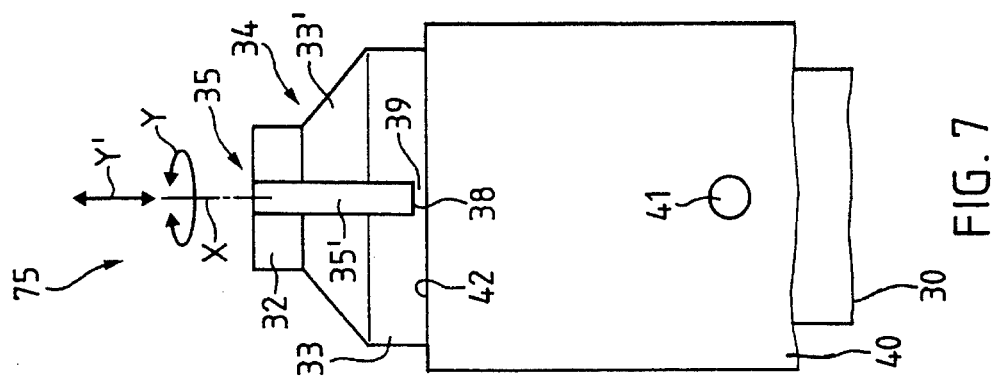
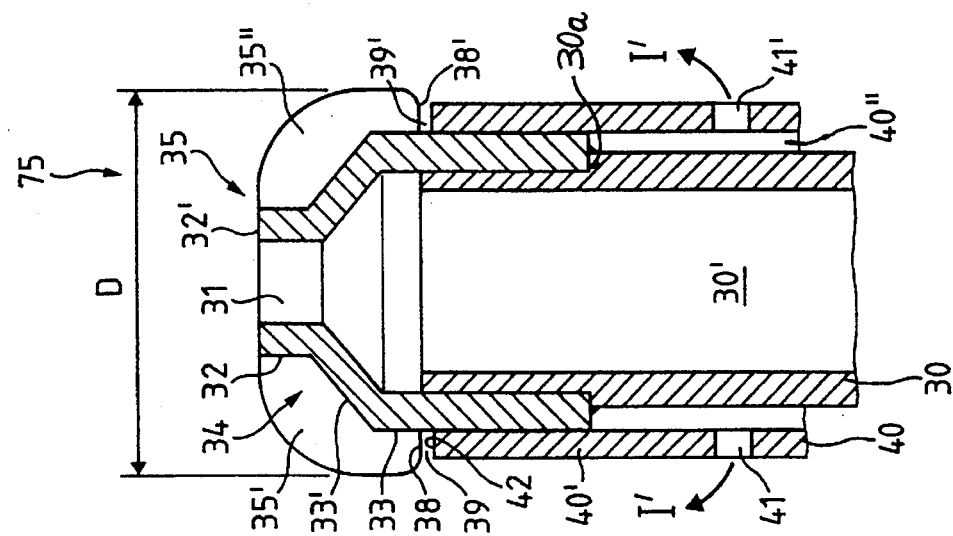
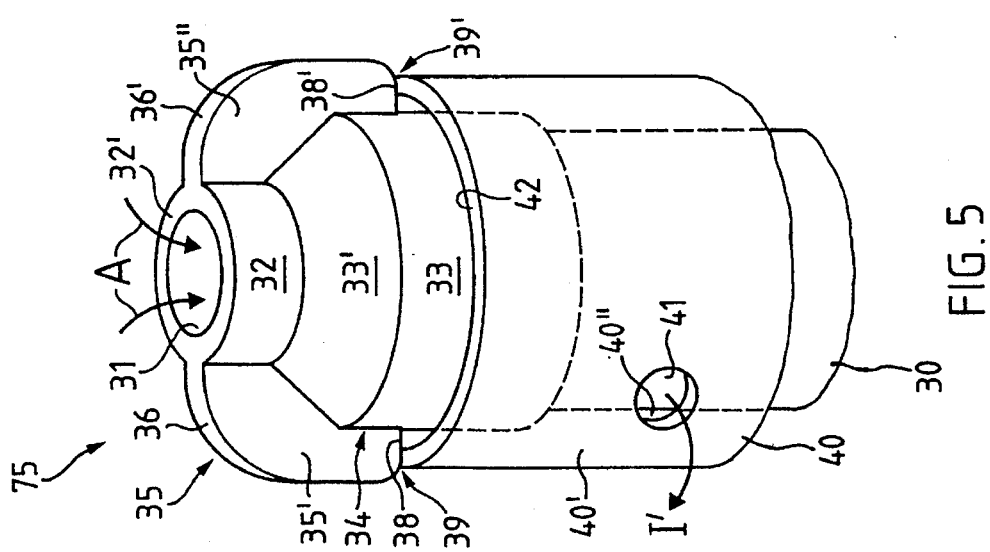

OPTHALMIC SURGICAL APPARATUS FOR MACERATING AND REMOVING THE LENS NUCLEUS FROM THE EYE OF A LIVING BEING

BACKGROUND OF THE INVENTION

The present invention refers to an ophthalmic surgical device for macerating the lens nucleus (cataract) in the eye as well as aspirating of particulate lens nucleus from the eye of a living being. In particular, the present invention is concerned with an ophthalmic surgical device of the type essentially including a housing in form of a handpiece that has a head piece for receiving a guide tube which coaxially supports a tubular probe. A drive mechanism is arranged within the housing for rotating about the longitudinal axis of the guide tube a cutting element which is supplied with irrigation fluid from an infusion conduit, with excess fluid being withdrawn together with lens particles by a suction pump via the tubular probe and via a suction line which is connected to the vacuum pump.

The lens (ocular) is part of the optical eye system of a living being. The primary function of the lens is the adjusting ability of the refractive power, i.e. the accommodation of the eye for close objects. The accommodation which is attained essentially by the zonule fibers in cooperation with the ciliary muscle to essentially modify the ellipsoid configuration of the lens is dependent from the constitution (flexibility) of the lens nucleus.

When the lens nucleus becomes clouded and/or sclerosed, a disease known as so-called gray cataract, the vision becomes significantly impaired. Cataracts are differentiated essentially between congenital cataracts or cataracts caused by trauma, disease, or age. Senile cataracts which may occur between ages 50 and 60 are characterized by the accumulation of metabolic products within the lens fibers and by a disturbance between the osmotic balance of the lens and the aqueous humor. Vision impairing opacity of the eye may also occur following ocular trauma through accidents or those associated with systemic diseases such as diabetes mellitus and scleroderma. In general, a cataract is removed by employing intracapsular extraction by which the clouded lens is completely removed and subsequently replaced by an artificial implant.

U.S. Pat. No. 4,320,761 discloses a surgical device for excision of tissue, in particular for removing the gray cataract from the eye of a living being. The surgical device includes essentially a housing which accommodates a D.C. motor powered by a D.C. battery. Threadably engaged to the housing is a head piece which receives a first hollow needle communicating with a suction pump. Secured in side-by-side relation to the first needle is a second needle which is connected to a source of irrigation fluid. A shaft driven by the motor extends through the first needle and terminates in a twisted cutting tool by which the cataract to be removed is comminuted while simultaneously introducing a washing fluid and discharged together with excess washing fluid.

German patent no. DE-A 4,080,594 describes an ophthalmic surgical instrument for comminuting and removing lens debris and includes a hand-held housing which supports a receptacle in operative connection with suitable drive means. Received in the receptacle is a hollow needle formed as an ultrasonic probe with a lumen connected with a suction line via a passageway traversing the receptacle. The hollow needle or ultrasonic probe is moved longitudinally exclusively at high frequency while at a same time a washing fluid is supplied via an annular channel to the forward end part of the ultrasonic probe which is provided with outlet openings. The washing fluid is withdrawn and removed together with lens debris via the lumen of the hollow needle from the anterior chamber of the eye.

Further ophthalmic surgical instruments in form of rotary drills for comminuting a lens nucleus and for removing lens debris are further known from U.S. Pat. Nos. 3,976,077 and 4,002,169.

SUMMARY OF THE INVENTION

It is an object of the present invention to provide an improved ophthalmic surgical device by which the clouded lens nucleus is emulsified and removed completely as a pulpy mass without injuring the inner wall of the capsule.

This object and others which will become apparent hereinafter are attained in accordance with the present invention by extending the tubular probe in axial direction beyond the guide tube to form a cutting instrument which includes at least two wing-like blades extending transversely to the longitudinal axis of the probe and terminates in an inlet opening which communicates with a suction chamber in the head piece of the housing for removing the macerated cataract, with the suction chamber being connected to the suction pump and sealed from the feed passageway via which irrigation fluid is supplied to the surgical site.

According to another feature of the present invention, the tubular probe is rotatable relative to the stationary guide tube about the common longitudinal axis and/or oscillated at a high frequency in direction of the longitudinal axis.

Suitably, the wing-like blades diametrically oppose each other and are attached to the tubular probe at a distance to a circular upper rim of the guide tube by a mounting which is traversed by the inlet opening. According to one embodiment, the mounting is of approximate funnel-shaped configuration, with a first cylindrical section secured to the tubular probe, a conical section connected to the first cylindrical section and followed by a second cylindrical section, the upper surface of which extends flush with the wing-like blades which are secured to the mounting along those parts of the mounting extending beyond the guide tube.

Suitably, the cutting instrument has a width which exceeds the outer diameter of the guide tube, and may be in the magnitude of about 1.6 mm.

BRIEF DESCRIPTION OF THE DRAWING

The above and other objects, features and advantages of the present invention will now be described in more detail with reference to the accompanying drawing in which:

FIG. 5 is an enlarged schematic perspective view of a first embodiment of a cutting instrument according to the invention;

FIG. 6 is a sectional view of the cutting instrument of FIG. 5;

FIG. 7 is a schematic side view of the cutting instrument of FIG. 5;

DETAILED DESCRIPTION OF PREFERRED EMBODIMENTS

Figure 1:
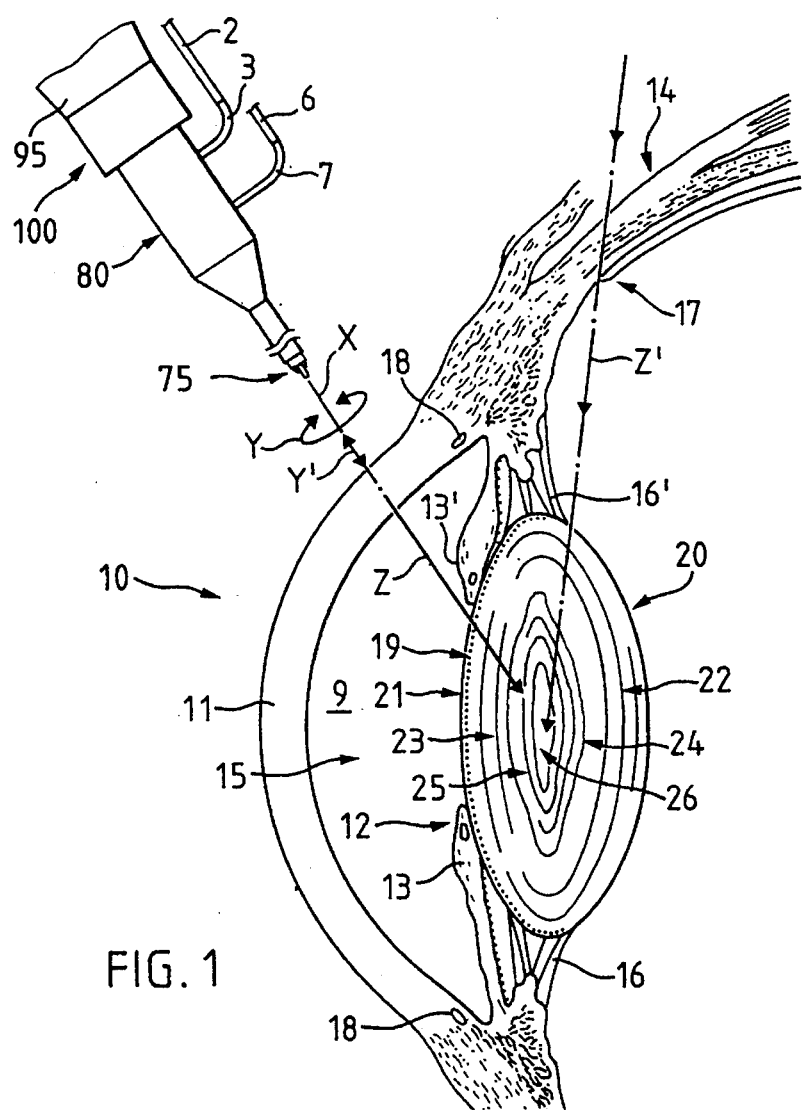
FIG. 1 is an enlarged schematic illustration of the forward eye section of a living being together with an ophthalmic surgical device according to the present invention for removing a cataract.

Turning now to the drawing, and in particular to FIG. 1, there is shown an enlarged forward section of a human eye, generally designated by reference numeral 10 and including the cornea 11, the anterior chamber 9, the iris generally designated by reference numeral 12 and including both circular areas 13, 13', the sclera 14, the pupil 15, the lens 20 (ocular) with the ciliary processes 16, 16' (zonule fibers), the pars plana generally designated by reference numeral 17 and the circular canal of Schlemm 8.

The lens 20 is a transparent, biconvex structure situated behind the iris 12 and the pupil 15, and the interior of the lens 20 is made up of a number of discontinuity zones illustrated schematically in FIG. 1. These discontinuity zones are subdivided essentially in three pads, that is an elastic capsule, a lens epithelium and the lens fibers. The capsule 19 of the lens is an elastic membrane that envelopes the entire lens. The lens epithelium 21 lies beneath the capsule 19 and extends only on the anterior surface of the lens up to about the equator where the lens epithelium cells 21 become transformed into lens fibers. The lens fiber is made up of anterior and posterior lens codex zone 22, anterior and posterior adult nucleus 23, anterior and posterior outer embryonic nucleus 24, anterior and posterior inner embryonic nucleus 25 and the lens center or nucleus 26.

As schematically illustrated in FIG. 1, the surgical procedure for removing a cataract is performed by an ophthalmic device which is generally designated by reference numeral 100. The ophthalmic surgical device 100 essentially includes an elongated housing 95 to form a handpiece which can be gripped by a user, and a head piece or fitting 80 for receiving a suitable cutting instrument 75. A drive unit (not shown) incorporated within the housing 95 is provided to rotate the cutting instrument 75 about a longitudinal axis X in direction of double arrow Y and to oscillate the cutting instrument 75 longitudinally (axis X) in direction of double arrow Y'. Although not shown in detail, the drive unit is preferably designed in such a manner that a so-called superimposition of the described motions and thus a combination of the oscillating and rotating motions is possible.

The surgical operation for removal of a clouded lens tissue or lens nucleus (cataract) encompasses in a first phase an expansion of the iris 12 through medication or through respectively hook-shaped iris retractors, and the formation of a small incision in the cornea 11. Subsequently, the ophthalmic surgical device 100 with the cutting instrument 75 is inserted in direction of arrow Z into the eye 10. The cutting instrument 75 is guided through the incision in the cornea 11 and an opening in the capsule 19 to reach the lens 20 for macerating the lens nucleus, with lens debris being simultaneously withdrawn in form of a pulpy mass from the capsule 19.

Persons skilled in the art will understand that the ophthalmic surgical device 100 may also be inserted through the pars plana 17 into the lens in a direction of arrow Z', as indicated in FIG. 1.

Figure 2:
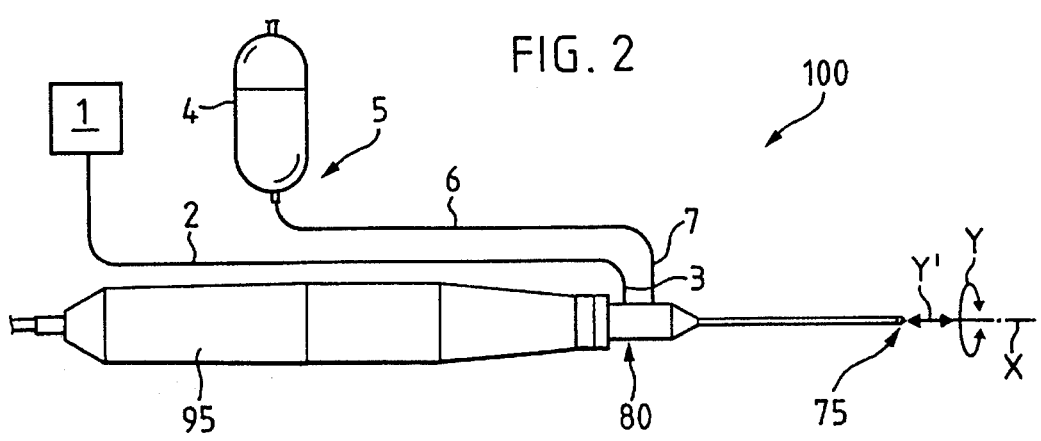
FIG. 2 is a schematic illustration of the ophthalmic surgical device according to FIG. 1.

Turning now to FIG. 2, there is shown a schematic illustration of the ophthalmic surgical device 100. The fitting 80 which is attached to the hand-held housing 95 is connected to a suction pump 1 via a suction tube 2 and to an infusion bottle 4 of an infusion unit, generally designated by reference numeral 5, via an infusion tube 6. Reference numerals 3 and 7 designate respective connectors on the fitting 80 for respective attachment of the suction tube 2 and infusion tube 6. Detachably secured to the tip of the fitting 80 is the cutting instrument 75.

Figure 3:
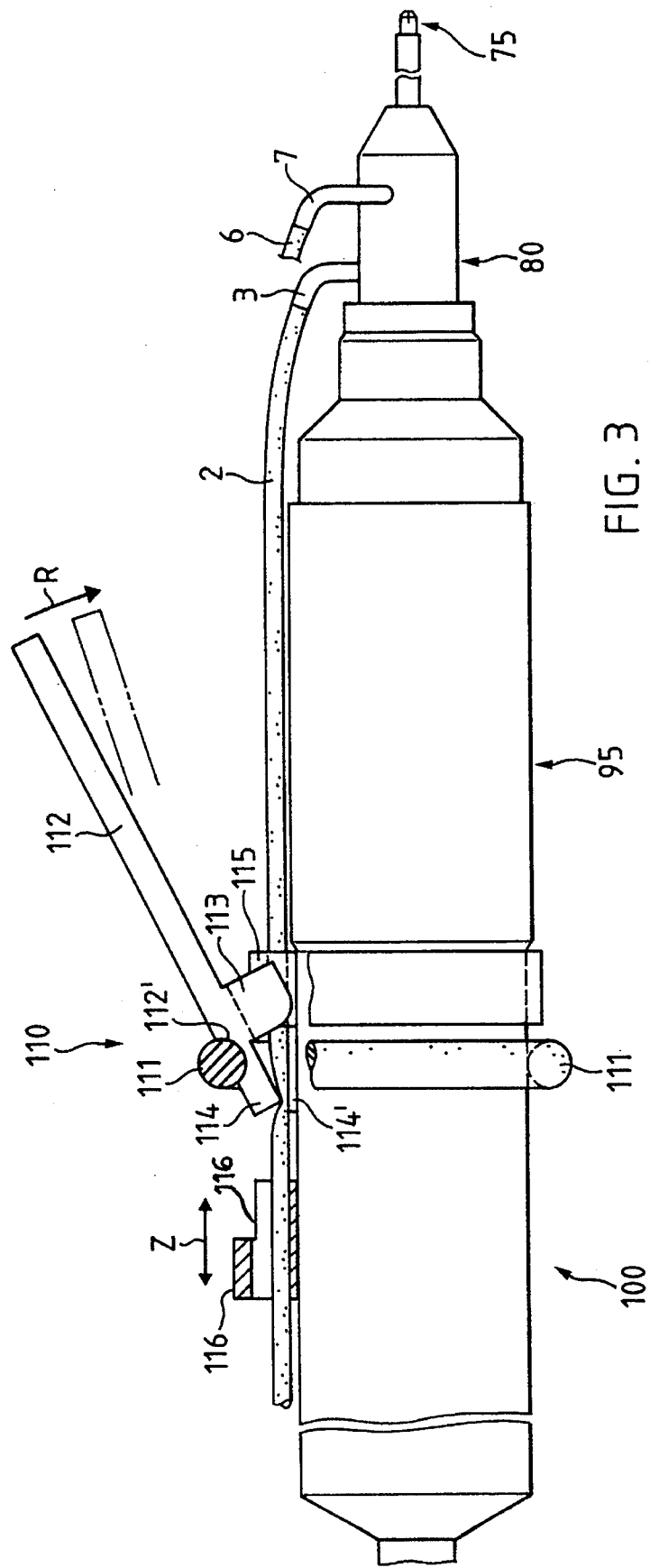
FIG. 3 is an enlarged schematical illustration of the ophthalmic surgical device according to FIG. 1, illustrating in detail a clamping mechanism for controlling flow of fluid through a suction line for withdrawal of lens debris.

FIG. 3 shows an enlarged view of the ophthalmic surgical device 100 with the housing 95 in form of e.g. a cylinder and the fitting 80 which is supported by the housing 95 and carries the cutting instrument 75. Mounted to the fitting 80 is the connector 3 for the suction tube 2, and at a distance from the connector 3 is the connector 7 for the infusion tube 6. Although not shown in detail, the attachment of the tubes 2 and 6 to the connectors 3 and 7 may be attained through any suitable means.

Mounted at a suitable location to the housing 95 is a clamping unit, generally designated by reference numeral 110 for controlling flow through the suction tube 2. The clamping unit 110 includes a mounting 115 which is secured at a suitable location to the housing 95. Pivoted to the mounting 115 is a bearing member 113 which projects at a right angle from a lever arm 112 at a distance from the tip of the lever arm 112. The section between the bearing member 113 and the tip of the lever arm 112 represents a compressor 114 by which the suction tube 2 can be constricted through suitable actuation of the lever arm 112 against the return force of a spring element. In the nonlimiting example of the clamping unit 110 in FIG. 3, the lever arm 112 is provided on its surface opposite to the bearing member 113 with an arched recess 112' for receiving e.g. an elastic O-ring 111 which has a relatively high resilient return force. Certainly, the O-ring 111 may be substituted by any functionally analogous spring element. Arranged opposite to the compressor 114 at the other side of the suction tube 2 is an abutment 114' which is suitably attached to the housing 95. Through actuation of the lever arm 112 in direction of arrow R, the compressor 114 becomes disengaged from the suction tube 2 so as to permit a connection the interior of the fitting 80 with the suction pump 1. A release of the lever arm 112 causes a movement of the compressor 114 towards the abutment 114' so that the suction tube 2 is cross-clamped to interrupt a flow of fluid therethrough, as shown in FIG. 3.

When being clamped, the section of the suction tube 2 located behind the compressor 114 is evacuated by the suction pump 1 to generate a vacuum within this section of the suction tube 2. Thus, an actuation of the lever arm 112 in direction of arrow R causes a sudden suction force at the tip of the cutting element 75 which allows even larger lens debris or adhering tissue particles to be properly withdrawn.

As further shown in FIG. 3, the clamping unit 110 further includes at a distance to the mounting 115 a locking element 116 which is guided along the housing 95 for movement in direction of double arrow Z to allow locking of the lever arm 112 in the position in which the lever arm 112 is disengaged from the suction tube 2. In the nonlimiting example of the locking element 116 in FIG. 3, the locking element 116 is provided with a recessed platform 116' for receiving the compressor 114. When the lever arm 112 is actuated in direction of arrow R to allow a flow of fluid through the suction tube 2, the locking element 116 is shifted underneath the compressor 114 for placement of the compressor 114 of the lever arm 112 on the platform 116'. By withdrawing the locking element 116 in opposite direction i.e. in direction away from the compressor 114, the lever arm 112 is released to allow engagement of the compressor 114 upon the suction tube 2, as shown in FIG. 3. Persons skilled in the art will understand that the locking element 116 may also be arranged directly on the suction tube 2 for movement in direction of double arrow Z and cooperation with the lever arm 112.

Figure 4:
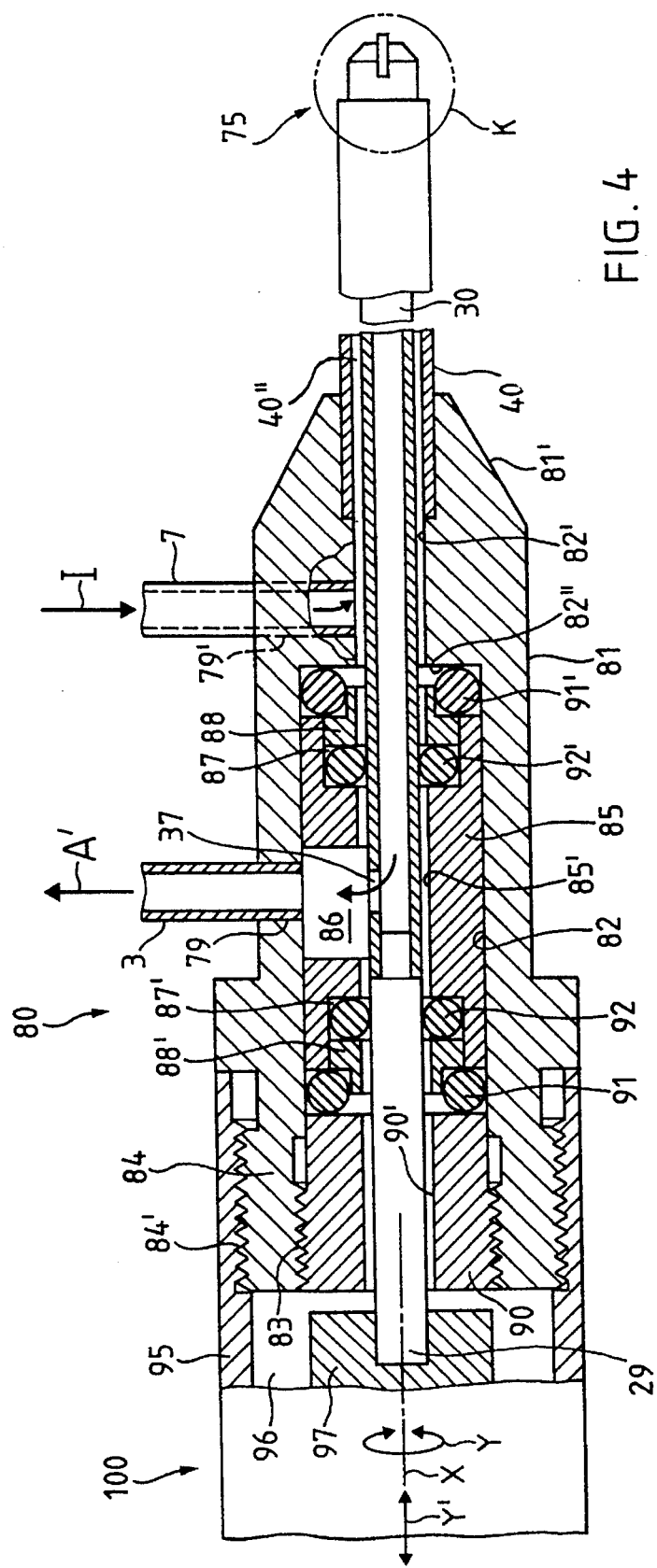
FIG. 4 is an enlarged fragmentary sectional view of the ophthalmic surgical device according to FIG. 1, illustrating in detail the head piece of the device for supporting the cutting instrument.

Turning now to FIG. 4, there is shown a more detailed sectional view of the fitting 80 on an enlarged scale. As can be seen from FIG. 4, the fitting 80 is of elongated configuration and includes a cylindrical section 81 which terminates at the forward end in a truncated cone-shaped end piece 81'. At its other end distant to the end piece 81', the cylindrical portion 81 is integrally connected to a threaded cap 84 which is provided with an internal thread 83 and with an external thread 84' for attachment to the hollow-cylindrical housing 95. Extending though the threaded cap 84 and terminating in the cylindrical portion 81 at a distance from the end piece 81' is an interior space 82 in form of a blind bore which is bounded by an end wall 82". In communication with the interior space 82 is an axial channel 82' which traverses the end piece 81'.

The cylindrical portion 81 of the fitting 80 is provided with two bores 79, 79' spaced from each other in axial direction for receiving and attachment of the connectors 3, 7.

Received in the interior space 82 of the fitting 80 is a cylindrical intermediary piece or sleeve-like insert 85 which is traversed by an axial bore 85' and includes a chamber 86 which is in communication with the suction tube 2 via the connector 3. At its opposing axial ends, the insert 85 is provided with stepped recesses 87, 87' of greater diameter than the bore 85'. Placed in each recess 87, 87' is an O-ring seal 92, 92' which is secured by a retainer ring 88, 88'. Each retainer ring 88, 88' is of L-shaped cross section for securing a further O-ring seal 91, 91' at the axial end of each recess 87, 87'. A bushing 90 is threadably engaged with the internal thread 83 of the cap 84 for mutually bracing the retainer ring 88, 88' and the insert 85 with the pertaining O-ring seals 91, 92 and 91', 92' relative to the end face 82" of the interior space 82 within the fitting 80.

As further shown in FIG. 4, the bushing 90 is provided with a bore 90' for allowing traversal of a drive shaft 29 having one end received in a coupling 97 and another end terminating in a nipple 29' for attachment of a tubular probe 30 in form of a hollow needle which extends through the channel 82' and the bore 85' of the insert 85 and supports the cutting instrument 75. Surrounding the tubular probe 30 is a guide tube 40 which is retained in the end piece 81' in a manner that a circular feed channel 40" is defined between the outer wall of the probe 30 and the inner wall of the guide tube 40. The feed channel 40" is suitably sealed from the suction chamber 86 by the O-rings 91', 92' and communicates via the connector 7 with the infusion tube 6 for allowing supply of irrigation fluid through the irrigation port I to the cutting instrument 75 which is detachably secured to the guide tube 40, as will be described furtherbelow.

Although not shown in detail in FIG. 4, the housing 95 accommodates a motor drive which is operatively connected to the coupling 97 for moving the drive shaft 29 and thus the probe 30 together with the cutting instrument 75 relative to the stationary guide tube 30 about the longitudinal axis X in direction of arrow Y and axially in direction of double arrow Y' at a frequency in the range of 200–1,000 Hz.

In elongation of the bore 79 of the cylindrical portion 81, the probe 30 is provided with at least one outlet opening 37 which is surrounded by the suction chamber 86 of the insert 85 so that the interior of the probe 30 communicates with the suction tube 2 via the suction chamber 86. Thus, it is ensured that the suction effect remains uninterrupted during rotation of the probe 30 as indicated by the arrow Y and/or motion in axial direction as indicated by double arrow Y' so that lens debris and tissue particles are continuously withdrawn by the suction pump 1 from the surgical site through the aspiration port A'.

Turning now to FIGS. 5–7, there are shown various illustrations of a first embodiment of the cutting instrument 75 for use in the ophthaimic surgical device 100 and indicated in FIG. 4 by circle K, with FIG. 5 showing a perspective illustration of the cutting instrument 75, FIG. 6 a sectional view thereof and FIG. 7 a side view thereof. The cutting instrument 75 includes the tubular probe 30 which is received coaxially in the guide tube 40, with the circular feed channel 40" (FIG. 6) being formed between the outer wall of the probe 30 and the inner wall of the guide tube 40.

The attachment of the cutting instrument 75 together with the probe 30 to the guide tube 40 is obtained via a mounting, generally designated by reference numeral 34 and including a first cylindrical section 33, an inwardly directed conical section 33' and a second cylindrical section 32 of reduced diameter which defines the inlet opening 31 into the interior of the probe 30. The first cylindrical section 33 is received in the end section of the feed channel 40" between the probe 30 and guide tube 40 and sits on a circumferential shoulder 30a of the probe 30. Suitably, the cylindrical section 33 is securely fixed to the probe 30, e.g. through a weld (laser welding) as indicated in FIG. 6. Connected to the mounting 34 at the sections projecting beyond the guide tube 40 is a cutting element, generally designated by reference numeral 35 and including at least two diametrically opposing wing-like blades 35', 35" which are received in respective slots of the mounting 34 and secured therein by e.g. laser welding. Both wing-like blades 35', 35" are provided with an essentially arched cutting edge 36, 36', as best seen in FIG. 5.

In the embodiment of the cutting instrument 75 as shown in FIGS. 5–7, both wing-like blades 35', 35" form with the upper circular surface 32' of the second cylindrical section 32 a flat area which is flush with the cutting edges 36, 36' abutting thereto. A gap 39, 39' is respectively defined between the annular upper rim 42 of the guide tube 40 and the opposing lower edge 38, 38' of the blades 35', 35".

The width D (outer dimension of the cutting element 35) as measured in radial direction of the blades 35', 35" may be in the range of about 1.6 mm and exceeds the outer diameter of the guide tube 40. Suitably, the outer diameter of the guide tube 40 is in the range of 1.4 mm–1.5 mm.

As the cylindrical section 33 of the mounting 34 is received in the end section of feed channel 40" and in order to allow a supply of irrigation fluid to the surgical site, the wall 40' of the guide tube 40 is provided with at least two diametrically opposing outlet bores 41, 41' at a distance to the mounting 34 to allow a flow of fluid from the irrigation port I via the feed channel 40" to the surgical site as indicated by arrow I' in FIGS. 5 and 6.

FIG. 7 indicates that the probe 30 as well as the mounting 34 together with the cutting element 35 are rotatable about a common axis X in direction of arrow Y relative to the stationary guide tube 40 and movable in axial direction relative to the guide tube 40 in direction of arrow Y' by means of the drive unit fitted in the housing 95.

Figure 10:
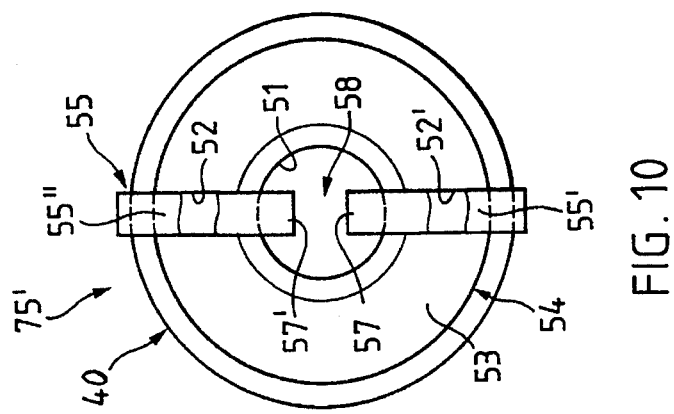
FIG. 10 is a top view of the cutting instrument of FIG. 8.
Figure 9:
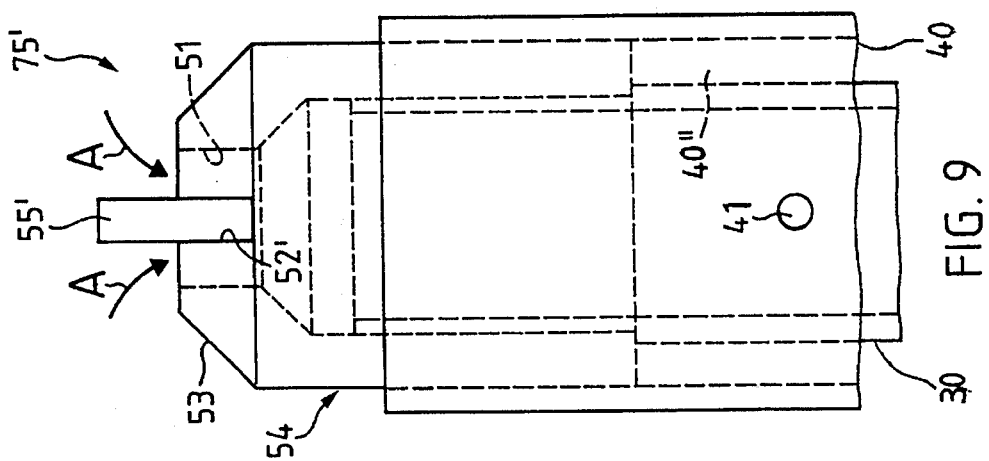
FIG. 9 is a schematic side view of the cutting instrument of FIG. 8.
Figure 8:
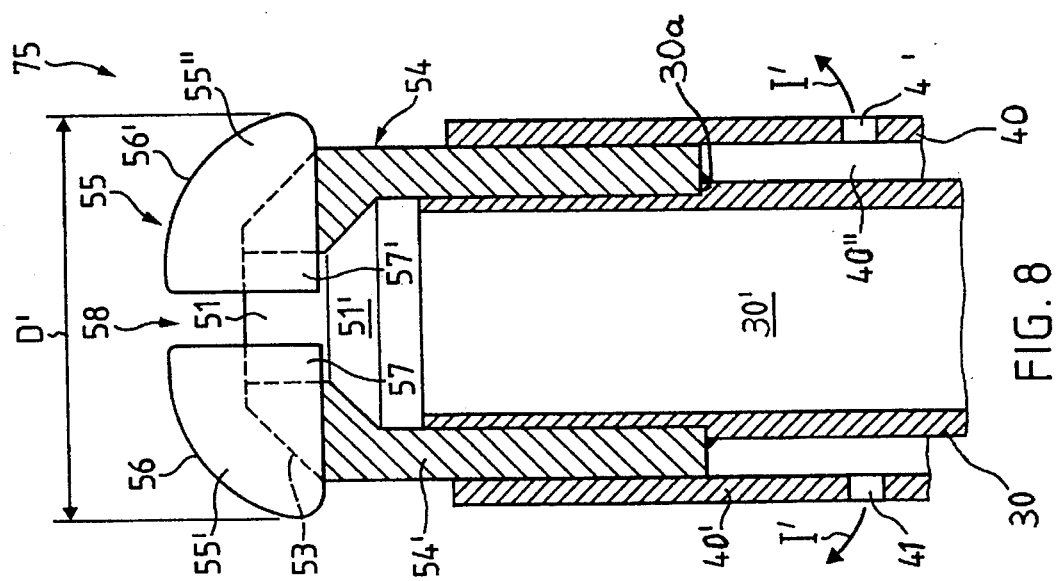
FIG. 8 is an enlarged sectional view of a second embodiment of a cutting instrument according to the invention.

FIGS. 8–10 show a second embodiment of the cutting instrument 75, with FIG. 8 illustrating a sectional view of the cutting instrument 75, FIG. 9 a side view thereof and FIG. 10 a top view thereof. For sake of simplicity and ease of understanding, same or corresponding elements are essentially indicated by the same reference numerals. The cutting instrument 75 of FIGS. 8–10 differs from the previous embodiment essentially in the configuration of the mounting now designated by reference numeral 54. The mounting 54 is provided with a cylindrical section 54' which is placed or inserted in the feed channel 40" between the tubular probe 30 and the surrounding guide tube 40 to rest on the shoulder 30a of the probe 30 and is secured to the probe 30 through laser welding. The cylindrical section 54' extends beyond the probe 30 and the guide tube 40 and terminates in a conical section 53 which is inwardly tapered to define an inlet opening 51 and an inner space 51'. The conical section 53 is provided with at least two diametrically opposing slots 52, 52' (FIG. 10) extending in axial direction of the mounting 54 for receiving the cutting element 55 in form of wing-like blades 55', 55". Both blades 55', 55" are radially extended by a prolongation 57, 57' to project into the inlet opening 51 and to define a gap 58 therebetween, as best seen in FIGS. 8 and 10. Each blade 55', 55" is provided with an arched cutting edge 56, 56' and extends with their cutting edges 56, 56' in axial direction at a slight distance above the circular area of the conical section 53.

Figure 11:
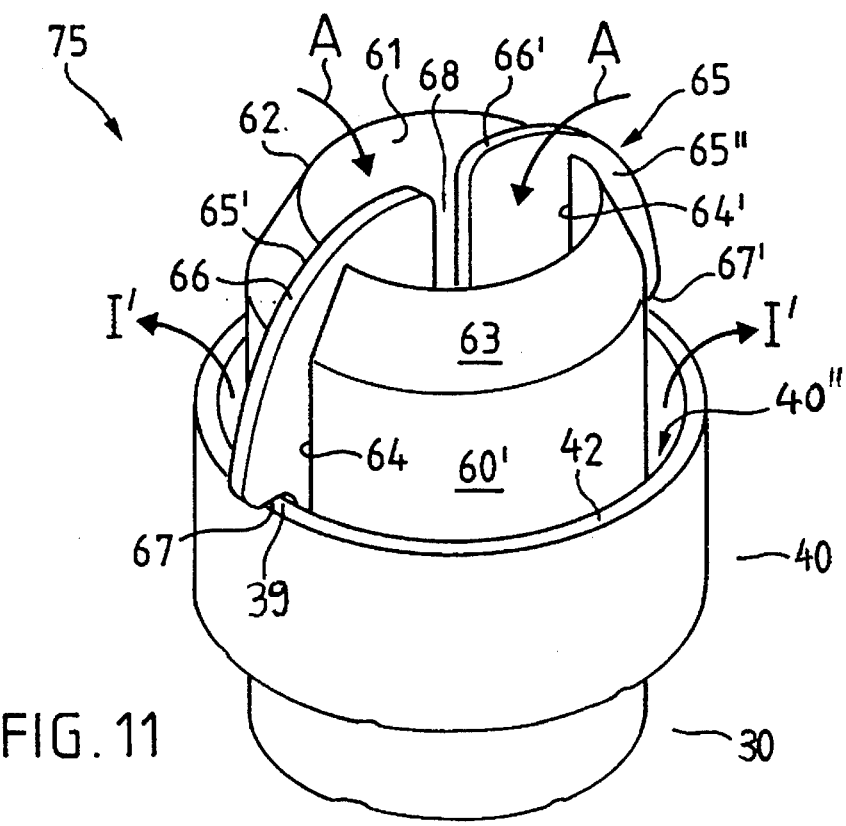
FIG. 11 is an enlarged perspective view of a third embodiment of a cutting instrument according to the invention.
Figure 12:
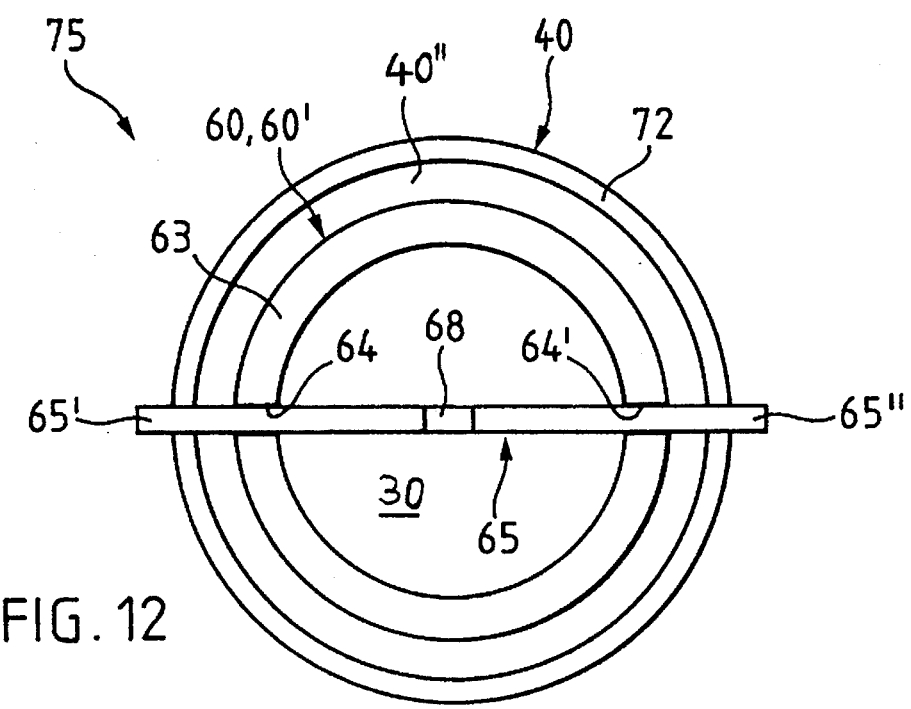
FIG. 12 is a top view of the cutting instrument of FIG. 11.
Figure 13:
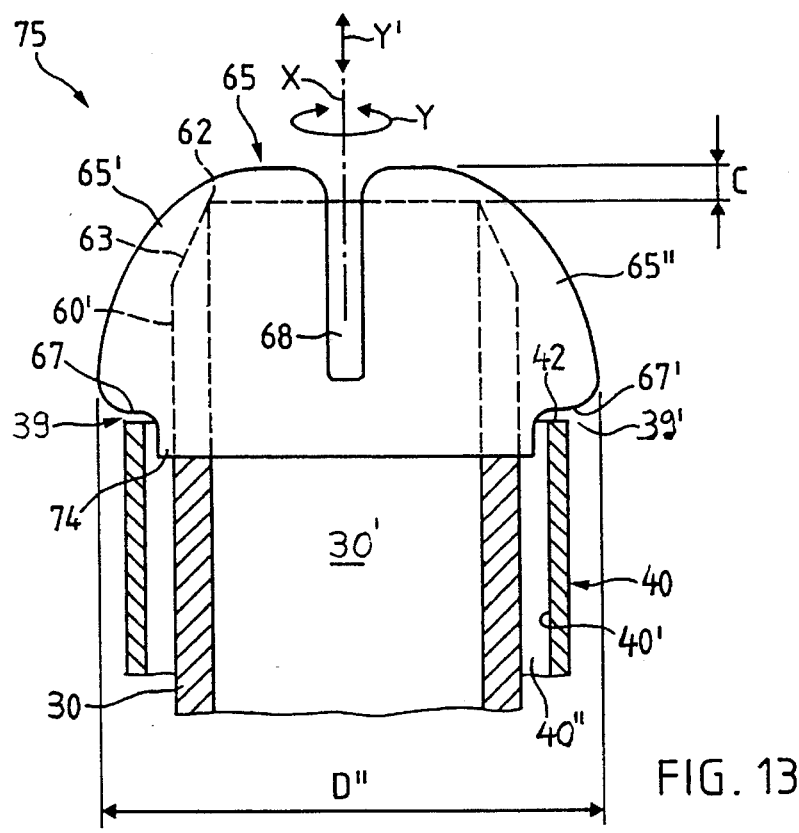
FIG. 13 is a partial sectional view of the cutting instrument of FIG. 11.

FIGS. 11 to 13 show a third embodiment of the cutting instrument 75, with FIG. 11 showing a perspective illustration of the cutting instrument 75, FIG. 12 a top view thereof and FIG. 13 a sectional view thereof. Again, for sake of simplicity and for ease of understanding, same or corresponding elements are essentially indicated by same reference numerals. In contrast to the first and second embodiments of the cutting instrument 75, the probe 30 is now extended in axial direction beyond the guide tube 40 by a prolongation 60' which terminated in a conical tip to form a beveled cutting area 63 with circular cutting edge 62. The prolongation 60' of the tubular probe 30 is provided with at least two diametrically opposed axial slots 64, 64' for receiving a cutting element, generally designated by reference numeral 65 and secured to the probe 60 preferably through laser welding.

The cutting element 65 is divided in two wing-like blades 65', 65" by a slot 68 which extends axially in direction of the probe 60 along a major portion of the cutting element 65. Both blades 65', 65" are provided with a cutting edge 66, 66' which extends in axial direction at a slight distance C above the circular cutting edge 62 at the tip of the extension 60' of the probe 60, as shown in particular in FIG. 13. The lower edge 67, 67' of the blades 65', 65" is spaced from the annular upper rim 42 of the guide tube 40 at a distance 39, 39', as shown in FIG. 13. FIG. 12 illustrates in particular the guide tube 40 which surrounds the coaxial probe 60 with the cutting element 65 received in the slots 64, 64' and with the cutting element 65 being partly divided by slot 68 to form the blades 65', 65".

As further shown by the enlarged sectional view of FIG. 13, the cutting element 65 is downwardly extended by a laterally inwardly recessed centering piece 74 which is spaced from the surrounding wall 40' of the guide tube 40 for placement of the cutting element 65 within the guide tube 40.

In the embodiment of FIGS. 11–13, irrigation fluid is supplied to the surgical site via the feed channel 40" in direction of arrow I' as shown in FIG. 11.

Figure 14:
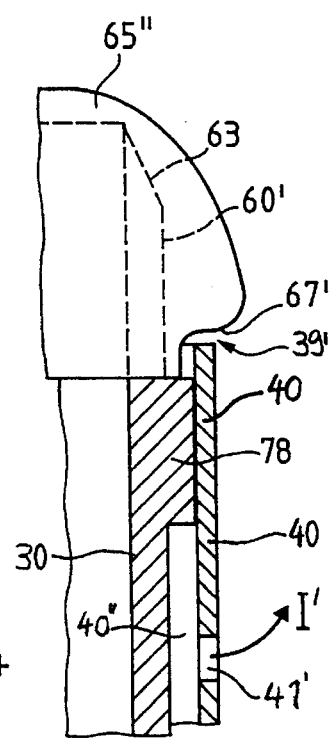
FIG. 14 is a fragmentary partly sectional view of a modification of the cutting instrument of FIG. 11.

Turning now to FIG. 14, there is shown a fragmentary partial sectional view of a variation of the third embodiment of the cutting instrument 75 according to FIGS. 11 to 13, with the difference residing in the configuration of the tubular probe 30. As shown in FIG. 14, the probe 30 is provided with a radial prolongation 78 near the rim of the guide tube 40 to upwardly close the feed channel 40" and for guidance along the inside surface of wall 40' of the guide tube 40. In order to supply irrigation fluid to the surgical site from the irrigation port I (FIG. 4), the guide tube 40 is provided with at least two outlet openings 41' (only one is shown in FIG. 14) for allowing irrigation fluid to exit the feed channel 40" in direction of I'.

In accordance with a nonlimiting example of the present invention, the outer diameter of the guide tube 40 is about 1.5 mm and the outer diameter of the inner probe 30 is about 1.0 mm. The width D of the cutting instrument 75 as measured across the cutting element 35, 55, 65 is preferably greater than the diameter of the guide tube 40 and may be in the range of about 1.6 mm. The indicated dimensions are given only for illustrative purposes and may be reduced if desired.

During surgical operation, an incision is made in the cornea 11 and the cutting instrument 75 is guided through the cornea 11 in direction of the lens 20. The rotation and oscillation of the cutting instrument 75 at a high frequency transforms the sclerosed lens nucleus into a pulpy mass which is withdrawn through aspiration by means of the suction pump 1. As described above, actuation of the lever arm 112 (FIG. 3) causes a sudden vacuum in the suction tube 2 so that excised lens debris is drawn through inlet opening 31 into the interior space 30' of the probe 30 and exits via outlet opening 37 and suction chamber 86 through suction tube 2. During excision of lens tissue, irrigation fluid is supplied through tube 6 and feed channel 40" to the surgical site to macerate the lens tissue. The milky opacity of the lens caused through emulsification in particular in the treated lens area is substituted through irrigating fluid to maintain the configuration of the capsule during withdrawal of the pulpy mass through the probe 30 so that a substantially unobstructed view of the cutting instrument 75 positioned in the lens 20 is ensured.

The essentially arched or wedged configuration of the blades with the cutting edges eliminates an unintentional injury of the capsule during surgery. Moreover, the particular configuration of the tip of cutting instrument ensures a withdrawal and removal of lens debris and pulpy lens mass during surgery into the center of the inlet opening 31 for discharge through the suction tube 2. Adhering tissue particles are sufficiently macerated by the blades and removed. Since the blades of the cutting instrument extend laterally beyond the outer diameter of the guide tube 40, a penetration into an extremely sclerosed lens nucleus (cataracts) is ensured.

As stated above, the cutting instrument 75 ensures a removal of detached, larger lens debris through simultaneous maceration and of the cell layer (cortex) to be detached at the transition from lens nucleus to lens sack through aspiration in direction of arrow A from the lens sack. The lens debris and the cell layer (cortex) are aspirated in the area of the inlet opening 31 and retained at the forward part of the cutting instrument 75 while simultaneously being comminuted and macerated by the rotating blades. The lens particles are then withdrawn through the inner space 30' of the tubular probe 30 via the outlet opening 37 in the rear end of the probe 30 into the suction chamber 86 and discharged through the suction tube 2 in direction of arrow A'.

Preferably, before carrying out the actual surgical operation i.e. before macerating the sclerosed lens nucleus, the inside of the cornea 11 with the endothelial cells is protected before the emulsification of the lens nucleus through injection of a suitable gel in order to attain a reliable protection of the cells during the entire surgery and to essentially eliminate complications caused by necrotic endothelial cells.

While the invention has been illustrated and described as embodied in an ophthalmic surgical device for macerating and removing the lens nucleus from the eye of a living being, it is not intended to be limited to the details shown since various modifications and structural changes may be made without departing in any way from the spirit of the present invention.

We claim:

1. An ophthalmic surgical device for macerating and removing the lens nucleus of the eye of a living being, comprising:

a housing defining an axis and being adapted for gripping by a user; and cutting means supported by said housing for macerating the lens nucleus, said cutting means including a tubular probe received coaxially within said housing, a cutting element extending in elongation of said tubular probe in axial direction beyond said housing in form of at least two rotatable wing-like blades oriented approximately transversely to the axis and defining an inlet opening in communication with said tubular probe, and a mounting attached to a forward position of said housing and secured to said tubular probe, said mounting being traversed by said inlet opening and supporting said wing-like blades, said housing having a first passageway for introducing a fluid to said wing-like blades and a second passageway suitably sealed from said first passageway for withdrawing macerated lens nucleus via said inlet opening and said tubular probe, wherein said mounting is of approximate funnel-shaped configuration, with a first cylindrical section secured to said tubular probe, a conical section having one end connected to said first cylindrical section and another end, and a second cylindrical section connected to said other end of said conical part and having an upper surface, said wing-like blades being attached to said mounting and having an upper surface which extends flush with said upper surface of said second cylindrical section.

2. Apparatus as defined in claim 1 wherein said wing-like blades diametrically oppose each other.

3. Apparatus as defined in claim 1 wherein said mounting includes a cylindrical section secured to said tubular probe and a conical end section connected to said cylindrical section for attachment of said wing-like blades, said wing-like blades being extended in radial direction so as to be spaced from each other at formation of a gap and including cutting edges arranged in axial direction at a slight distance above a circular area of said conical end section.

4. Apparatus as defined in claim 1 wherein said wing-like blades of said cutting element are partially spaced from each other by an axial slot and secured to said tubular probe at an extension thereof which projects beyond said housing, said extension having a tapered cutting area with a circular cutting edge at a free end thereof.

5. Apparatus as defined in claim 4 wherein said wing-like blades of said cutting element slightly extend beyond said circular cutting edge of said extension of said tubular probe and include a centering element radially spaced at a slight distance from an inner wall of said housing.

6. Apparatus as defined in claim 1 wherein each of said wing-like blades is provided with a tapered cutting edge extending from one housing-proximate end in axial direction toward said inlet opening.

7. Apparatus as defined in claim 6 wherein each of said wing-like blades tapers toward said inlet opening in form of a circular arc.

8. Apparatus as defined in claim 6 wherein each of said wing-like blades tapers toward said inlet opening in a wedge-shaped manner.

9. Apparatus as defined in claim 1 wherein said housing has an inside wall extending extending at a distance to said tubular probe for defining said first passageway between said inside wall of said housing and an outside wall of said tubular probe.

10. Apparatus as defined in claim 1 wherein said housing has a forward end receiving a guide tube extending axially in prolongation of said housing and surrounding said tubular probe at a distance thereto for extending said first passageway.

11. Apparatus as defined in claim 10 wherein said cutting element has a width and said guide tube has an outer diameter, said width of said cutting element exceeding said outer diameter of said guide tube.

12. An ophthalmic surgical device for macerating the lens nucleus in the eye and for removing particles of the macerated lens nucleus from the eye of a living being, comprising:

a housing defining an axis and being adapted for gripping by a user;

a fitting attached to one axial end of said housing and including a forward end supporting a guide tube having at least one outlet, said fitting accommodating a chamber;

cutting means supported by said fitting and including a tubular probe received coaxially in said guide tube to define a feed channel therebetween, a cutting element extending said tubular probe in axial direction and including at least two rotatable wing-like blades oriented approximately transversely to the axis, said cutting element including an inlet opening extending in axial direction of said probe in proximity of said wing-like blades, said cutting means further including a mounting which is traversed by said inlet opening and secured to said tubular probe for supporting said wing-like blades at a distance to a circular upper rim of said guide tube, said tubular probe being provided with an outlet opening in communication with said chamber which is sealed from said feed channel;

fluid supply means operatively connected to said fitting for feeding a fluid to said cutting element via said feed channel and said one outlet of said guide tube; and suction means communicating with said chamber of said fitting for drawing excess fluid and particles of the lens nucleus via said outlet opening of said tubular probe into said chamber of said fitting, wherein said mounting is of approximate funnel-shaped configuration, with a first cylindrical section secured to said tubular probe, a conical section having one end connected to said first cylindrical section and another end, and a second cylindrical section connected to said other end of said conical part and having an upper surface, said wing-like blades being attached to said mounting and having an upper surface which extends flush with said upper surface of said second cylindrical section.

13. Apparatus as defined in claim 12 wherein said guide tube is stationarily secured in said fitting, and further comprising drive means for moving said cutting means relative to said guide tube about said axis and in direction of said axis.

14. Apparatus as defined in claim 13 wherein said drive means oscillates said cutting means at a high frequency.

15. Apparatus as defined in claim 12 wherein said wing-like blades diametrically oppose each other.

16. Apparatus as defined in claim 15 wherein said mounting includes a cylindrical section secured to said tubular probe and a conical end section connected to said cylindrical section for attachment of said wing-like blades, said wing-like blades being extended in radial direction so as to be spaced from each other at formation of a gap and including cutting edges arranged in axial direction at a slight distance above a circular area of said conical end section.

17. Apparatus as defined in claim 12 wherein said wing-like blades of said cutting element are partially spaced from each other by an axial slot and secured to said tubular probe at an extension thereof which projects beyond said guide tube, said extension having a tapered cutting area with a circular cutting edge at a free end thereof.

18. Apparatus as defined in claim 17 wherein said wing-like blades of said cutting element slightly extend beyond said circular cutting edge of said extension of said tubular probe and include a centering element radially spaced at a slight distance from an inner wall of said guide tube.

19. Apparatus as defined in claim 12 wherein each of said wing-like blades is provided with a tapered cutting edge extending from one end facing said guide tube in axial direction toward said inlet opening.

20. Apparatus as defined in claim 19 wherein each of said wing-like blades tapers toward said inlet opening in form of a circular arc.

21. Apparatus as defined in claim 19 wherein each of said wing-like blades tapers toward said inlet opening in a wedge-shaped manner.

22. Apparatus as defined in claim 12 wherein said cutting element has a width and said guide tube has an outer diameter, said width of said cutting element exceeding said outer diameter of said guide tube.

23. Apparatus as defined in claim 22 wherein said width is about 1.6 mm.

* * * * *

UNITED STATES PATENT AND TRADEMARK OFFICE
CERTIFICATE OF CORRECTION

PATENT NO. : 5,487,747

DATED : January 30, 1996

INVENTOR(S) : Robert Stegmann et al

It is certified that error appears in the above-identified patent and that said Letters Patent is hereby corrected as shown below:

On the title page, item [75], change "Stagmann" to --Stegmann--.

Signed and Sealed this

Seventh Day of May, 1996

Attest:

BRUCE LEHMAN

*Attesting Officer*   *Commissioner of Patents and Trademarks*